United States Patent
Okamura (10) Patent No.: US 7,787,592 B2
(45) Date of Patent: Aug. 31, 2010

(54) RADIOGRAPHIC APPARATUS AND RADIATION DETECTION SIGNAL PROCESSING METHOD

(75) Inventor: Shoichi Okamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 12/280,339

(22) PCT Filed: Feb. 23, 2006

(86) PCT No.: PCT/JP2006/303276

§ 371 (c)(1),
(2), (4) Date: Aug. 21, 2008

(87) PCT Pub. No.: WO2007/096968

PCT Pub. Date: Aug. 30, 2007

(65) Prior Publication Data

US 2009/0010392 A1   Jan. 8, 2009

(51) Int. Cl.
   H05G 1/64      (2006.01)
   G01N 23/04     (2006.01)
   H01L 27/146    (2006.01)
   G06K 9/36      (2006.01)
   G06K 9/40      (2006.01)

(52) U.S. Cl. ............... 378/98.8; 378/62; 378/98.12; 250/370.09; 382/131; 382/265; 382/275

(58) Field of Classification Search ............ 378/4, 378/11, 12, 19, 62, 98, 98.8, 98.12; 382/128, 382/130–132, 265, 275; 250/370.01, 370.08, 250/370.09, 371
See application file for complete search history.

(56) References Cited

U.S. PATENT DOCUMENTS

| | | | | |
|---|---|---|---|---|
| 4,794,531 A * | 12/1988 | Morishita et al. | ............ | 382/132 |
| 5,249,123 A | 9/1993 | Hsieh | | |
| 5,452,338 A * | 9/1995 | Granfors et al. | .......... | 378/98.11 |
| 5,563,421 A | 10/1996 | Lee et al. | | |
| 6,496,605 B1 * | 12/2002 | Osa | ............................ | 382/268 |
| 7,113,565 B2 * | 9/2006 | Endo | ............................ | 378/62 |
| 2003/0223539 A1 * | 12/2003 | Granfors et al. | ............ | 378/98.8 |

(Continued)

FOREIGN PATENT DOCUMENTS

JP   09-009153 A   1/1997

(Continued)

OTHER PUBLICATIONS

International Search Report for the Application No. PCT/JP2006/303276 mailed Mar. 20, 2006.

*Primary Examiner*—Edward J Glick
*Assistant Examiner*—Anastasia Midkiff
(74) *Attorney, Agent, or Firm*—Cheng Law Group, PLLC (57) ABSTRACT

A radiographic apparatus according to this invention, when carrying out recursive computation, pixel groups consisting of detection pixels respectively corresponding to positions on a radiation detection device are sorted into locations subjected to the recursive computation and locations exempted from the recursive computation. For the locations subjected to the recursive computation, lag-behind parts are removed by the recursive computation to obtain corrected radiation detection signals. The recursive computation is not carried out at least for the locations exempted from the recursive computation. The lag-behind parts can be removed from the radiation detection signals, with a calculation amount for the recursive computation reduced by an amount corresponding to the recursive computation excluded.

14 Claims, 6 Drawing Sheets

U.S. PATENT DOCUMENTS

| | | | |
|---|---|---|---|
| 2004/0156481 A1* | 8/2004 | Okamura et al. | 378/901 |
| 2005/0031070 A1* | 2/2005 | Okamura et al. | 378/22 |
| 2008/0315105 A1* | 12/2008 | Partain et al. | 250/370.08 |

FOREIGN PATENT DOCUMENTS

| | | | |
|---|---|---|---|
| JP | 2004-242741 A | 9/2004 |
| JP | 2004-321346 A | 11/2004 |
| JP | 2006-006387 A | 1/2006 |

* cited by examiner

RADIOGRAPHIC APPARATUS AND RADIATION DETECTION SIGNAL PROCESSING METHOD

TECHNICAL FIELD

This invention relates to a radiographic apparatus for medical or industrial use and a radiation detection signal processing method, for obtaining radiographic images based on radiation detection signals outputted at predetermined sampling time intervals from a radiation detecting device as radiation is emitted to an object under examination. More particularly, the invention relates to a technique for eliminating time lags, due to the radiation detecting device, of the radiation detection signals taken from the radiation detecting device.

BACKGROUND ART

In a medical X-ray diagnostic apparatus which is a typical example of radiographic apparatus, a flat panel X-ray detector (hereinafter called "FPD" as appropriate) has recently been used as an X-ray detecting device for detecting X-ray penetration images of a patient resulting from X-ray emission from an X-ray tube. The FPD includes numerous semiconductor or other X-ray detecting elements arranged longitudinally and transversely on an X-ray detecting surface.

That is, the X-ray diagnostic apparatus is constructed to obtain, based on X-ray detection signals for one X-ray image taken at sampling time intervals from the FPD as a patient is irradiated with X rays from the X-ray tube, an X-ray image corresponding to an X-ray penetration image of the patient for every period between sampling intervals. The use of the FPD is advantageous in terms of apparatus construction and image processing since the FPD is lighter and less prone to complicated detecting distortions than the image intensifier used heretofore.

However, the FPD has a drawback of causing time lags whose adverse influence appears in X-ray images. Specifically, when X-ray detection signals are taken from the FPD at short sampling time intervals, the remainder of a signal not picked up adds to a next X-ray detection signal as a lag-behind part. Thus, where X-ray detection signals for one image are taken from the FPD at 30 sampling intervals per second to create X-ray images for dynamic display, the lag-behind part appears as an after-image on a preceding screen to produce a double image. This results in an inconvenience such as blurring of dynamic images.

U.S. Pat. No. 5,249,123 discloses a proposal to solve the problem of the time lag caused by the FPD in acquiring computer tomographic images (CT images). This proposed technique employs a computation for eliminating a lag-behind part from each of radiation detection signals taken from an FPD at sampling time intervals $\Delta t$.

That is, in the above U.S. patent, a lag-behind part included in each of the radiation detection signals taken at the sampling time intervals is assumed due to an impulse response formed of a plurality of exponential functions, and the following equation is used to derive radiation detection signal $x_k$ with a lag-behind part removed from radiation detection signal $y_k$:

$$x_k = [y_k - \Sigma_{n=1}^{N}\{\alpha_n \cdot [1-\exp(T_n)] \cdot \exp(T_n) \cdot S_{nk}\}]/\Sigma_{n=1}^{N}\beta_n$$

in which $T_n = -\Delta t/\tau_n$, $S_{nk} = x_{k-1} + \exp(T_n) \cdot S_{n(k-1)}$, and $\beta_n = \alpha_n \cdot [1-\exp(T_n)]$, where $\Delta t$: sampling intervals;

k: subscript representing a k-th point of time in a sampling time series;

N: the number of exponential functions with different time constants forming the impulse response;

n: subscript representing one of the exponential functions forming the impulse response;

$\alpha_n$: intensity of exponential function n; and $\tau_n$ attenuation time constant of exponential function n.

Inventors herein have tried the computation technique proposed in the above U.S. patent. However, the only result obtained is that the above technique cannot avoid artifacts due to the time lag and satisfactory X-ray images cannot be obtained. It has been confirmed that the time lag due to the FPD is not eliminated (Patent Document 1).

Then, Inventors have previously proposed a technique in Unexamined Patent Publication No. 2004-242741. In dealing with the time lag of the FPD, this technique removes a lag-behind part due to an impulse response based on the following recursive equations a-c:

$$X_k = Y_k - \Sigma_{n=1}^{N}[\alpha_n \cdot [1-\exp(T_n)] \cdot \exp(T_n) \cdot S_{nk}] \quad \text{a}$$

$$T_n = -\Delta t/\tau_n \quad \text{b}$$

$$S_{nk} = X_{k-1} + \exp(T_n) \cdot S_{n(k-1)} \quad \text{c}$$

where $\Delta t$: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n;

$S_{n0} = 0$; and $X_0 = 0$.

In this recursive computation, coefficients of the impulse response of the FPD, N, $\alpha_n$ and $\tau_n$, are determined in advance. With the coefficients fixed, X-ray detection signal $Y_k$ is applied to equations a-c, thereby obtaining a lag-free X-ray detection signal $X_k$ (Patent Document 2). The above correction for removing the lag-behind part is also called "lag correction".

Besides the above technique of Patent Document 2, there is a technique of using backlight to reduce long time constant components of lag-behind parts (see Patent Document 3, for example).

[Patent Document 1]

U.S. Pat. No. 5,249,123 (mathematical expressions in the specification and the drawings)

[Patent Document 2]

Unexamined Patent Publication No. 2004-242741 (mathematical expressions in the specification and the drawings)

[Patent Document 3]

Unexamined Patent Publication H9-9153 (pages 3-8, FIG. 1)

DISCLOSURE OF THE INVENTION

Problem to be Solved by the Invention

However, a 17-inch size FPD, for example, has 3072×3072 pixels arranged vertically and horizontally, and the above technique of Patent Document 2 requires an enormous calculation amount for recursive computation. Thus, in fluoroscopy of dynamic images, a binning operation is carried out to add pixels as a measure for reducing calculation amounts. In a binning operation to combine 2×2 vertical and horizontal pixels into one, for example, the number of pixels is decreased to one fourth by the binning operation, thereby reducing the calculation amount to one fourth. In a binning operation to combine 4×2 pixels, i.e. 4 vertical pixels and 2 horizontal pixels, into one, the number of pixels is decreased to one eighth by the binning operation, thereby reducing the calculation amount to one eighth.

However, if the backlight of Patent Document 3 noted above is deleted out of the necessity to keep down cost, the amount of time constant components of lag-behind parts (also called "lag components") will increase. As a measure against this situation, it is conceivable to increase the number of time constant components of the lag-behind parts used for lag correction. However, an increase in the number of components will increase a calculation amount.

This invention has been made having regard to the state of the art noted above, and its object is to provide a radiographic apparatus and a radiation detection signal processing method capable of reducing a calculation amount, and eliminating time lags, due to a radiation detecting device, from radiation detection signals taken from the radiation detecting device.

Means for Solving the Problem

To fulfill the above object, this invention provides the following construction.

A radiographic apparatus of this invention is a radiographic apparatus for obtaining radiographic images based on radiation detection signals, comprising a radiation emitting device for emitting radiation toward an object under examination, a radiation detecting device for detecting radiation transmitted through the object under examination, and a signal sampling device for taking radiation detection signals from the radiation detecting device at predetermined sampling time intervals, said apparatus being constructed to obtain radiographic images based on the radiation detection signals outputted from the radiation detecting device at the predetermined sampling time intervals as radiation is emitted to the object under examination, said apparatus further comprising a time lag removing device for removing lag-behind parts from the radiation detection signals by a recursive computation, on an assumption that a lag-behind part included in each of said radiation detection signals taken at the predetermined sampling time intervals is due to an impulse response formed of a single or a plurality of exponential functions with different attenuation time constants; and a pixel group sorting device for sorting pixel groups consisting of detection pixels respectively corresponding to positions on said radiation detection device, into locations subjected to said recursive computation and locations exempted from the recursive computation; wherein, for the locations subjected to the recursive computation, said time lag removing device removes lag-behind parts by the recursive computation to obtain corrected radiation detection signals.

In the radiographic apparatus according to this invention, the time lag removing device removes lag-behind parts included in the radiation detection signals outputted from the radiation detecting device at the predetermined sampling time intervals as radiation is emitted to the object under examination by the radiation emitting device, as being due to an impulse response formed of a single or a plurality of exponential functions with different attenuation time constants. A lag-behind part is removed from each radiation detection signal through a recursive computation. The recursive computation is carried out as follows. The pixel group sorting device sorts pixel groups consisting of detection pixels respectively corresponding to positions on the radiation detection device, into locations subjected to the recursive computation and locations exempted from the recursive computation. For the locations subjected to the recursive computation, the time lag removing device removes lag-behind parts by the recursive computation. Radiographic images are acquired from corrected radiation detection signals obtained.

Thus, according to the radiographic apparatus of this invention, the recursive computation is not carried out at least for the locations exempted from the recursive computation. Consequently, the lag-behind parts can be removed from the radiation detection signals, with a calculation amount for the recursive computation reduced by an amount corresponding to the recursive computation excluded.

A radiation detection signal processing method of this invention is a radiation detection signal processing method for taking, at predetermined sampling time intervals, radiation detection signals detected after irradiation of an object under examination, and carrying out signal processing to obtain radiographic images based on the radiation detection signals outputted at the sampling time intervals, the radiation detection signal processing method removing lag-behind parts from the radiation detection signals by a recursive computation, on an assumption that a lag-behind part included in each of said radiation detection signals taken at the predetermined sampling time intervals is due to an impulse response formed of a single or a plurality of exponential functions with different attenuation time constants, wherein pixel groups consisting of detection pixels respectively corresponding to positions on a radiation detection device, which detects radiation and outputs said radiation detection signals, are sorted into locations subjected to said recursive computation and locations exempted from the recursive computation; and, for the locations subjected to the recursive computation, lag-behind parts are removed by the recursive computation to obtain corrected radiation detection signals.

According to the radiation detection signal processing method of this invention, when the recursive computation is carried out, the pixel groups consisting of detection pixels respectively corresponding to positions on the radiation detection device are sorted into locations subjected to the recursive computation and locations exempted from the recursive computation. For the locations subjected to the recursive computation, lag-behind parts are removed by the recursive computation to obtain corrected radiation detection signals. The recursive computation is not carried out at least for the locations exempted from the recursive computation. Consequently, the lag-behind parts can be removed from the radiation detection signals, with a calculation amount for the recursive computation reduced by an amount corresponding to the recursive computation excluded. Since the locations subjected to the recursive computation are reduced, the calculation amount can be reduced without extensively changing the conventional apparatus construction. An advantage is provided also that lag correction, which is a correction for removing lag-behind parts, can be carried out using an increased number of time constant components.

In one example of these radiographic apparatus and radiation detection signal processing noted above, when part of pixel groups arranged in one predetermined direction are regarded as lines, the locations exempted from the recursive computation are set as predetermined lines, and the locations subjected to the recursive computation are set as lines other than the predetermined lines. With such settings, a division is made in relation to the lines, whereby the lines can be divided into the locations subjected to the recursive computation and the locations not subjected to the recursive computation.

In one example of the above lines, the following setting is possible when the radiation detection device has a two-dimensional arrangement of a plurality of radiation detecting elements respectively corresponding to pixels, a plurality of gate bus lines connected to the respective radiation detecting elements for switching control of said radiation detecting elements, and data bus lines extending perpendicular to said gate bus lines and connected to the respective radiation detecting elements for reading said radiation detection signals from the radiation detecting elements.

That is, the locations exempted from said recursive computation may be set as predetermined data bus lines, and the locations subjected to the recursive computation may be set as data bus lines other than the predetermined data bus lines. With such setting, a division is made in relation to the data bus lines, whereby the lines can be divided into the locations subjected to the recursive computation and the locations exempted from the recursive computation. Since the data bus lines extend along the reading direction, the predetermined data bus lines can easily be sorted out at a reading time.

In one example of such data bus lines, the following division can also be made. That is, adjacent data bus lines may be sorted alternately into the locations exempted from the recursive computation and the locations subjected to the recursive computation.

In another example of these radiographic apparatus and radiation detection signal processing noted above, for the locations exempted from the recursive computation, lag-behind parts are removed to obtain corrected radiation detection signals by using a value based on results of the recursive computation for the locations present adjacent the locations and having undergone the recursive computation. By removing lag-behind parts for the locations exempted from the recursive computation in this way, the effect of lag correction which is a correction for removing lag-behind parts can be secured similarly to the locations having undergone the recursive computation, and the effect is hardly impaired.

In one example of removing lag-behind parts for the locations exempted from the recursive computation in this way, the value based on results of the recursive computation is an amount of statistics based on results of the recursive computation. By removing lag-behind parts using such an amount of statistics, corrected radiation detection signals can be acquired with increased reliability, also for the locations exempted from the recursive computation. One example of the above amount of statistics is an average value of results of the recursive computation. The following is one example of using such an average value.

For the locations subjected to said recursive computation, the recursive computation is carried out for removing the lag-behind parts from the radiation detection signals, based on the following equations A-C:

$$X_k = Y_k - \Sigma_{n=1}^{N}[S_{nk}] \qquad \text{A}$$

$$T_n = -\Delta t / \tau_n \qquad \text{B}$$

$$S_{nk} = \exp(T_n) \cdot \{\alpha_n \cdot [1 - \exp(T_n)] \cdot \exp(T_n) \cdot S_{n(k-1)}\} \qquad \text{C}$$

where $\Delta t$: the sampling time interval;

k: a subscript representing a k-th point of time in a sampling time series;

$Y_k$: a radiation detection signal taken at the k-th sampling time;

$X_k$: a corrected radiation detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$ an attenuation time constant of exponential function n;

to determine the initial values for the recursive computation as in the following equation D:

$$X_0 = 0, S_{n0} = \gamma_n \cdot Y_0 \qquad \text{D}$$

where $\gamma_n$: residual rate of component n of certain attenuation time constant $\tau_n$, and $Y_0$: lag signal value remaining at the radiation non-emission time serving as the base point for the recursive computation; and to obtain the corrected radiation detection signals by removing the lag-behind parts based on said impulse response derived from said equations A-C with conditions of the initial values determined from said equation D; and for the locations exempted from said recursive computation, assuming results of said recursive computation to be $\Sigma_{n=1}^{N}[S_{nk}]$ in said equation A, an average value of $\Sigma_{n=1}^{N}[S_{nk}]$ for the locations present adjacent the locations and having undergone the recursive computation is used to remove the lag-behind parts and obtain the corrected X-ray detection signals.

EFFECTS OF THE INVENTION

With the radiographic apparatus and radiation detection signal processing method according to this invention, the recursive computation is not carried out at least for the locations exempted from the recursive computation. Consequently, the lag-behind parts can be removed from the radiation detection signals, with a calculation amount for the recursive computation reduced by an amount corresponding to the recursive computation excluded.

DESCRIPTION OF REFERENCES

1 ... X-ray tube
2 ... FPD (flat panel X-ray detector)
3 ... A/D converter
11 ... time lag remover
12 ... pixel group sorter
22 ... X-ray detecting elements
26 ... gate bus lines
29 ... data bus lines
M ... patient

BEST MODE FOR CARRYING OUT THE INVENTION

A pixel group sorting device is provided for sorting pixel groups consisting of detection pixels respectively corresponding to positions on an FPD (flat panel X-ray detector), into locations subjected to a recursive computation (data bus lines of the FPD) and locations exempted from the recursive computation (data bus lines of the FPD). For the locations subjected to the recursive computation, lag-behind parts are removed by recursive computation to obtain corrected X-ray detection signals. The recursive computation is not carried out at least for the locations exempted from the recursive computation. Thus, the object is fulfilled to remove the lag-behind parts from the X-ray detection signals, with a calculation amount for the recursive computation reduced by an amount corresponding to the recursive computation excluded.

Embodiment

Figure 1:
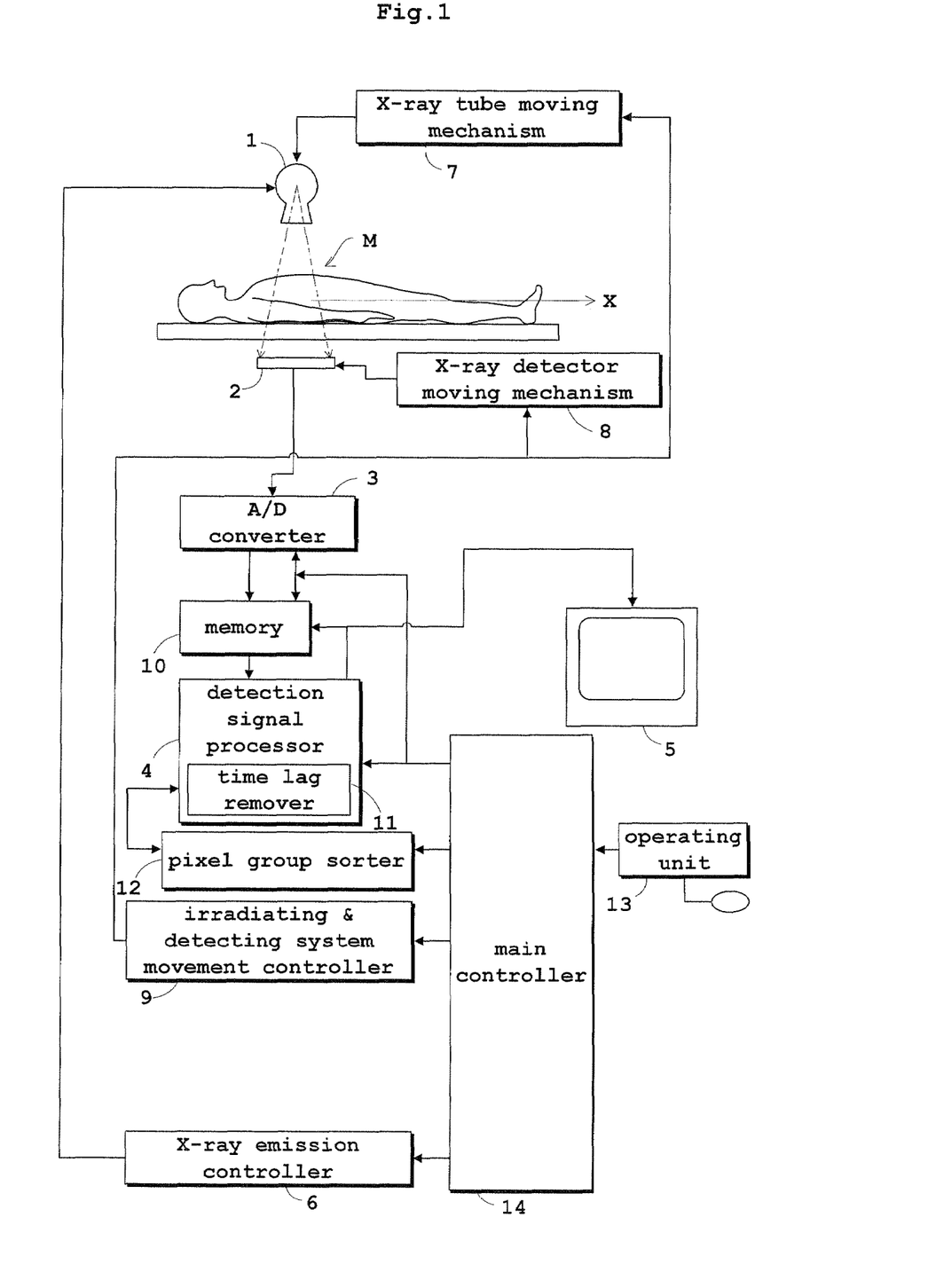
FIG. 1 is a block diagram showing an overall construction of a fluoroscopic apparatus according to an embodiment.

An embodiment of this invention will be described with reference to the drawings. FIG. 1 is a block diagram showing an outline of a fluoroscopic apparatus according to the embodiment.

As shown in FIG. 1, the fluoroscopic apparatus includes an X-ray tube 1 for emitting X rays toward a patient M, an FPD 2 (flat panel X-ray detector) for detecting X rays transmitted through the patient M, an analog-to-digital converter 3 for digitizing X-ray detection signals taken from the FPD 2 at predetermined sampling time intervals Δt, a detection signal processor 4 for creating X-ray images based on X-ray detection signals outputted from the analog-to-digital converter 3, and an image monitor 5 for displaying the X-ray images acquired by the detection signal processor 4. That is, the apparatus in this embodiment is constructed to acquire X-ray images from the X-ray detection signals taken from the FPD 2 by the analog-to-digital converter 3 as the patient M is irradiated with X rays, and display the acquired X-ray images on the screen of the image monitor 5. Each component of this apparatus will particularly be described hereinafter. The X-ray tube 1 corresponds to the radiation emitting device in this invention. The FPD 2 corresponds to the radiation detecting device in this invention. The analog-to-digital converter 3 corresponds to the signal sampling device in this invention. The X-ray detection signals correspond to the radiation detection signals in this invention. The X-ray images correspond to the radiographic images in this invention.

The X-ray tube 1 and FPD 2 are opposed to each other across the patient M. Specifically, the X-ray tube 1 and FPD 2 are opposed to each other such that, in time of X-ray radiography, the X-ray tube 1 is controlled by an X-ray emission controller 6 to emit X rays in the form of a cone beam to the patient M, and at the same time, penetration X-ray images of the patient M produced by the X-ray emission are projected to an X-ray detecting surface of FPD 2.

The X-ray tube 1 and FPD 2 are movable back and forth along the patient M by an X-ray tube moving mechanism 7 and an X-ray detector moving mechanism 8, respectively. In moving the X-ray tube 1 and FPD 2, the X-ray tube moving mechanism 7 and X-ray detector moving mechanism 8 are controlled by an irradiating and detecting system movement controller 9 to move the X-ray tube 1 and FPD 2 together as opposed to each other, with the center of emission of X rays constantly in agreement with the center of the X-ray detecting surface of FPD 2. Movement of the X-ray tube 1 and FPD 2 results in variations in the position of the patient M irradiated with X rays, hence movement of a radiographed site.

Figure 2:
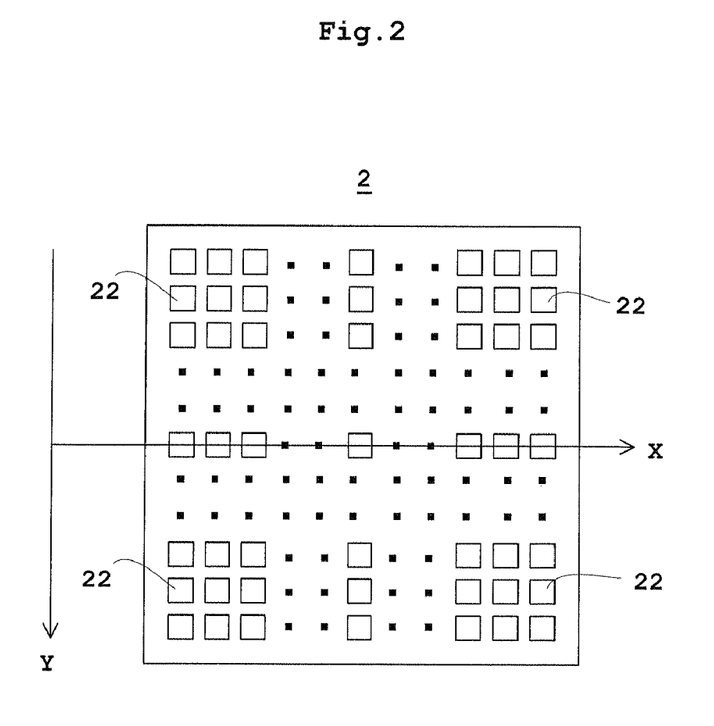
FIG. 2 is a plan view showing a construction of an FPD used in the apparatus according to the embodiment.

As shown in FIG. 2, the FPD 2 has numerous X-ray detecting elements 22 arranged longitudinally and transversely along the direction X of the body axis of patient M and the direction Y perpendicular to the body axis, on the X-ray detecting surface to which penetration X-ray images from the patient M are projected. For example, X-ray detecting elements 22 are arranged to form a matrix of 3072 by 3072 on the X-ray detecting surface about 17 inches long and 17 inches wide. Each X-ray detecting element 22 of FPD 2 corresponds to one pixel in an X-ray image created by the detection signal processor 4. Based on the X-ray detection signals taken from the FPD 2, the detection signal processor 4 creates an X-ray image corresponding to a penetration X-ray image projected to the X-ray detecting surface. The X-ray detecting elements 22 correspond to the radiation detecting elements in this invention.

The analog-to-digital converter 3 continually takes X-ray detection signals for each X-ray image at sampling time intervals Δt, and stores the X-ray detection signals for X-ray image creation in a memory 10 disposed downstream of the converter 3. An operation for sampling (extracting) the X-ray detection signals is started before X-ray emission.

Figure 3:
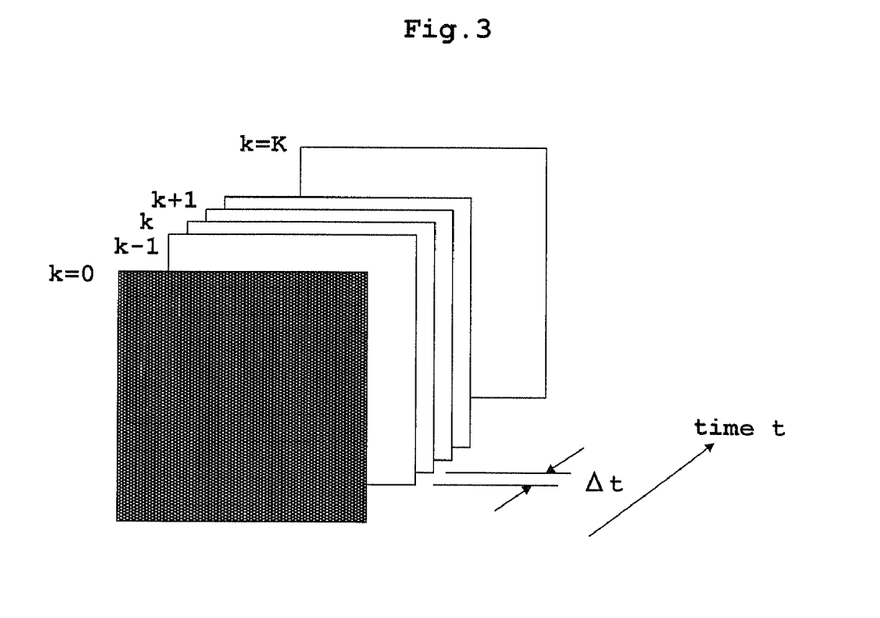
FIG. 3 is a schematic view showing a state of sampling X-ray detection signals during X-ray radiography by the apparatus according to the embodiment.

That is, as shown in FIG. 3, all X-ray detection signals for a penetration X-ray image are collected at each period between the sampling intervals Δt, and are successively stored in the memory 10. The sampling of X-ray detection signals by the analog-to-digital converter 3 before an emission of X rays may be started manually by the operator or automatically as interlocked with a command for X-ray emission.

Figure 4:
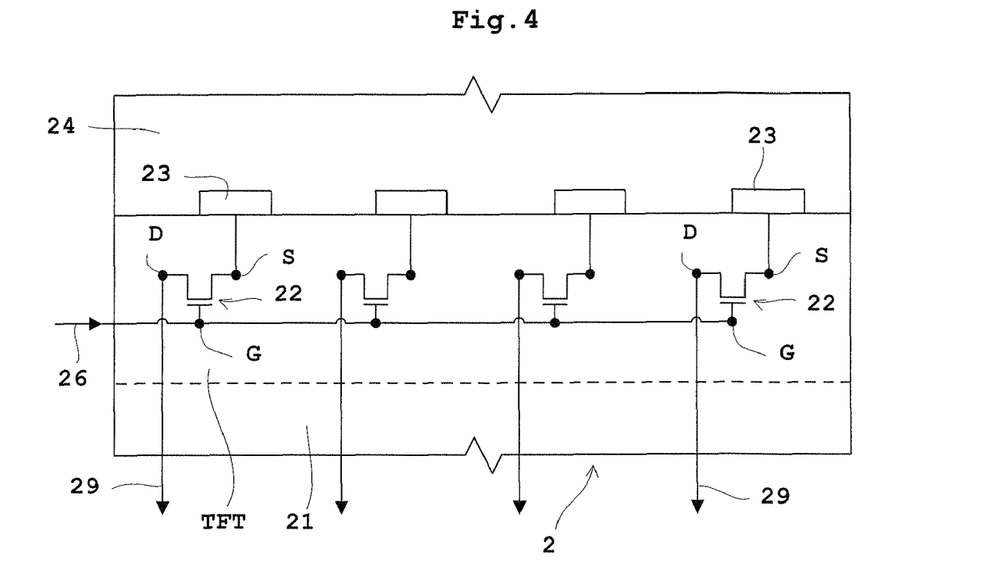
FIG. 4 is an equivalent circuit of the FPD seen in a sectional view.
Figure 5:
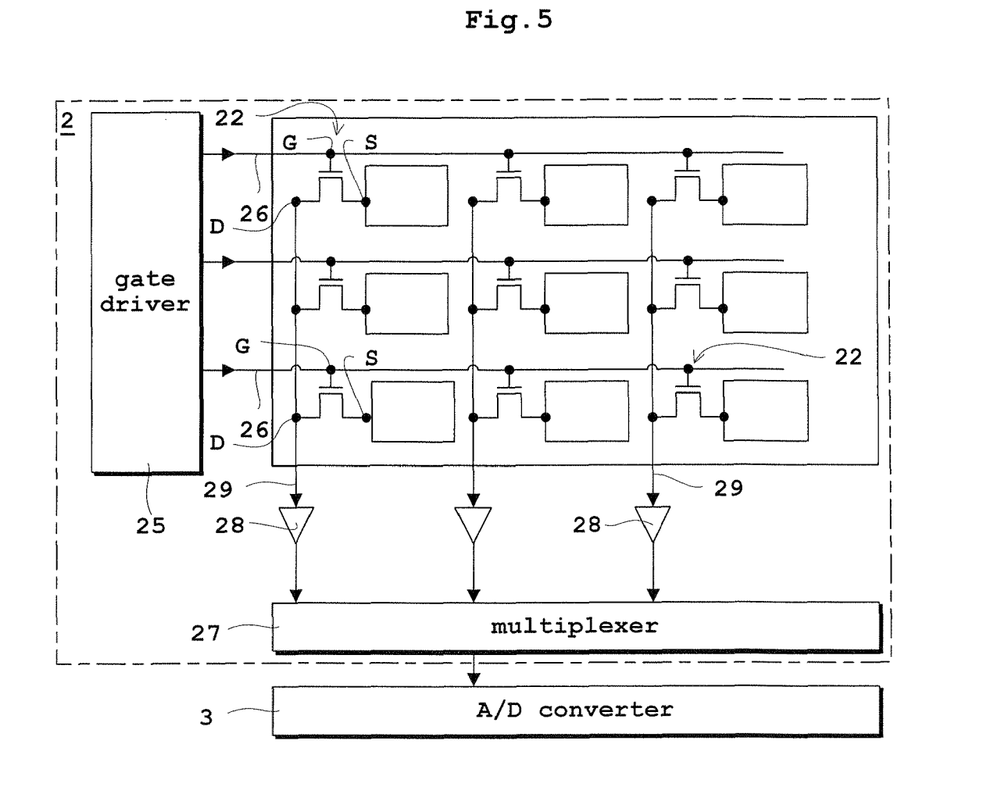
FIG. 5 is an equivalent circuit of the FPD seen in a plan view.

A more specific construction of FPD 2 will be described. As shown in FIG. 4, the FPD 2 includes a glass substrate 21, and thin film transistors TFT formed on the glass substrate 21. As shown in FIGS. 4 and 5, the thin film transistors TFT comprise the numerous X-ray detecting elements 22 noted above. The X-ray detecting elements 22 are formed separate from one another for respective carrier collecting electrodes 23. The X-ray detecting elements 22 act as switching elements.

As shown in FIG. 4, an X-ray sensitive semiconductor 24 is laminated on the carrier collecting electrodes 23. As shown in FIGS. 4 and 5, the carrier collecting electrodes 23 are connected to the sources S of the X-ray detecting elements 22. A plurality of gate bus lines 26 extend from a gate driver 25, and are connected to the gates G of the X-ray detecting elements 22. On the other hand, as shown in FIG. 5, a plurality of data bus lines 29 are connected through amplifiers 28 to a multiplexer 27 for collecting charge signals and outputting them as one. As shown in FIGS. 4 and 5, the data bus lines 29 are connected to the drains D of the X-ray detecting elements 22.

With a bias voltage applied to a common electrode not shown, the gates of the X-ray detecting elements 11 are turned on by applying thereto (or reducing to 0V) the voltage of the gate bus lines 26. The carrier collecting electrodes 23 output charge signals (carriers) converted from X rays incident on the detection surface through the X-ray sensitive semiconductor 24, to the data bus lines 29 through the sources S and drains D of the X-ray detecting elements 22. The charge signals are provisionally stored in capacitors (not shown) until the X-ray detecting elements 22 are turned on. The amplifiers 28 amplify the charge signals read out to the data bus lines 29, and the multiplexer 27 collects the charge signals, and outputs them as one charge signal. The analog-to-digital converter 3 noted above digitizes the outputted charge signal, and outputs it as an X-ray detection signal. Thus, the gate bus lines 26 carry out switching control of the X-ray detecting elements 22, while the data bus lines 29 read X-ray detection signals (charge signals in analog state) from the X-ray detecting elements 22.

To summarize the above, the FPD 2 has a plurality of X-ray detecting elements 22 respectively corresponding to pixels and arranged two-dimensionally, a plurality of gate bus lines 26 connected to the X-ray detecting elements 22 for carrying out switching control of the X-ray detecting elements 22, and data bus lines 29 extending perpendicular to the gate bus lines 26 and connected to the X-ray detecting elements 22 for reading X-ray detection signals from the X-ray detecting elements 22. The gate bus lines 26 correspond to the gate bus lines in this invention. The data bus lines 29 correspond to the data bus lines in this invention.

As shown in FIG. 1, the fluoroscopic apparatus in this embodiment includes a time lag remover 11 for computing corrected radiation detection signals free from time lags, which are removed from the X-ray detection signals by a recursive computation process, and a pixel group sorter 12 for sorting into locations subjected to a recursive computation and locations exempted from the recursive computation. The time lag remover 11 corresponds to the time lag removing device in this invention. The pixel group sorter 12 corresponds to the pixel group sorting device in this invention.

A time lag is included in each of the X-ray detection signals fetched at the sampling time intervals from the FPD 2. The time lag is removed from each X-ray detection signal by the above recursive computation process based on an assumption that the time lag included in each of the X-ray detection signals taken at the sampling time intervals from the FPD 2 is due to an impulse response formed of one or a plurality of exponential functions with different attenuation time constants.

In doing so, the pixel group sorter 12 sorts pixel groups consisting of detected pixels respectively corresponding to positions of the X-ray detecting elements 22 of FPD 2, into the above-noted locations subjected to the recursive computation and locations exempted from the recursive computation. The time lag remover 11 removes lag-behind parts by recursive computation from the locations subjected to the recursive computation, and obtains corrected X-ray detection signals.

Figure 8:
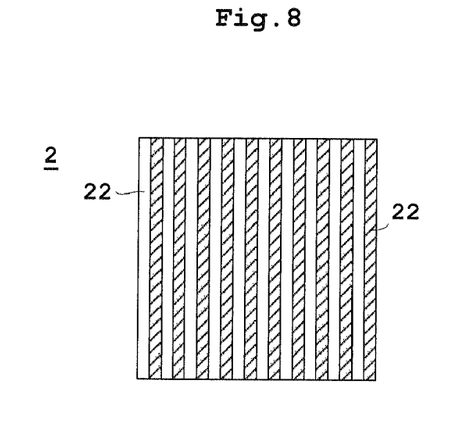
FIG. 8 is a schematic view showing adjacent data bus lines divided alternately into locations for which no recursive computation is carried out and locations for which the recursive computation is carried out.

In this embodiment, for sorting into the locations subjected to the recursive computation and locations exempted from the recursive computation, as shown in FIG. 8, the adjacent data bus lines 29 are sorted alternately into the locations subjected to the recursive computation and locations exempted from the recursive computation. In FIG. 8, data bus lines 29 subjected to the recursive computation are shown in hatches, while data bus lines 29 exempted from the recursive computation are shown in blank. When the data bus lines 29 subjected to the recursive computation are set to those even-numbered in order, the data bus lines 29 exempted from the recursive computation are set to those odd-numbered in order. Conversely, when the data bus lines 29 subjected to the recursive computation are set to those odd-numbered in order, the data bus lines 29 exempted from the recursive computation are set to those even-numbered in order. Setting of the data bus lines 29 subjected to or exempted from the recursive computation is not limited to odd numbers or even numbers.

In this embodiment, the time lag remover 11 obtains corrected X-ray detection signals by removing lag-behind parts for the locations exempted from the recursive computation using a value based on results of the recursive computation carried out for locations adjacent to the above locations and subjected to the recursive computation. As noted above, the adjacent data bus lines 29 are sorted alternately into the locations subjected to the recursive computation and locations exempted from the recursive computation. Therefore, preferred examples of data bus lines 29 adjacent to the data bus lines 29 exempted from the recursive computation, and of data bus lines 29 subjected to the recursive computation, are two data bus lines 29 (hatched parts in FIG. 8) present at opposite sides of each data bus line 29 (blank parts in FIG. 8) exempted from the recursive computation. In this embodiment, therefore, the recursive computation is carried out first for the data bus lines 29 of the hatched parts in FIG. 8, to remove lag-behind parts and obtain corrected X-ray detection signals. Then, a value based on results of the recursive computation is used to remove lag-behind parts and obtain corrected X-ray detection signals for the data bus line 29 of the blank parts in FIG. 8 (without carrying out the recursive computation).

In this embodiment, the value based on results of the recursive computation will be described taking, for example, an amount of statistics based on results of the recursive computation. Further, the amount of statistics based on results of the recursive computation will be described taking, for example, an average value of results of the recursive computation. The average value of results of the recursive computation will be described later.

On the other hand, in this embodiment, an initial value for the recursive computation is determined based on a lag signal value remaining at a base point of the recursive computation. The base point of the recursive computation here refers to an X-ray non-emission time (k=0) for a first frame. The lag signal value remaining at a base point of the recursive computation refers to lag signal value $Y_0$ remaining at the X-ray non-emission time. By the recursive computation based on the initial value determined, the time lag remover 11 removes lag-behind parts and obtains corrected X-ray detection signals (that is, for the data bus lines 29 subjected to the recursive computation).

Figure 9:
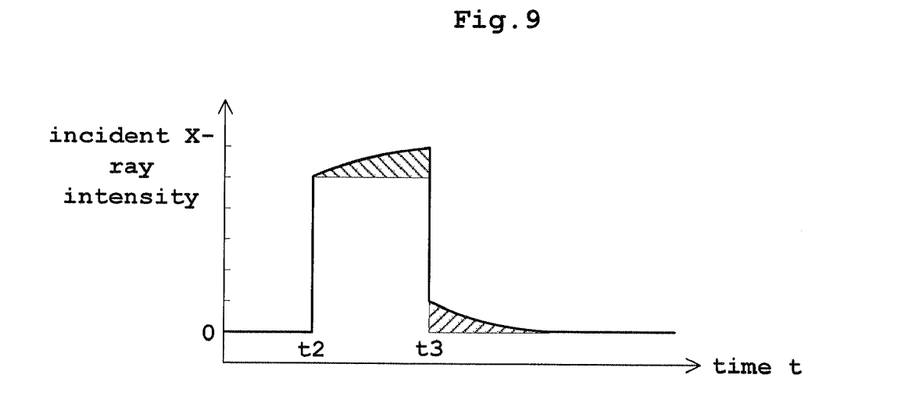
FIG. 9 is a view showing time lags corresponding to a state of radiation incidence.

With the FPD 2, an X-ray detection signal generated at each point of time, as shown in FIG. 9, includes signals corresponding to preceding X-ray emissions and remaining as a lag-behind part (see a hatched part in FIG. 9). The time lag remover 11 removes this lag-behind part to produce a corrected, lag-free X-ray detection signal. Based on such lag-free X-ray detection signals, the detection signal processor 4 creates an X-ray image corresponding to a penetration X-ray image projected to the X-ray detecting surface.

Specifically, the time lag remover 11 performs a recursive computation process for removing a lag-behind part from each X-ray detection signal by using the following equations A-C:

$$X_k = Y_k - \Sigma_{n=1}^{N} [S_{nk}] \quad\quad A$$

$$T_n = -\Delta t / \tau_n \quad\quad B$$

$$S_{nk} = \exp(T_n) \cdot \{\alpha_n \cdot [1-\exp(T_n)] \cdot \exp(T_n) \cdot S_{n(k-1)}\} \quad\quad C$$

where $\Delta t$: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n.

The second term et seq. at the right side in equation A, i.e. "$S_{nk} = \exp(T_n) \cdot \{\alpha_n \cdot [1-\exp(T_n)] \cdot \exp(T_n) \cdot S_{n(k-1)}\}$" in equation C, corresponds to the lag-behind part. Thus, the apparatus in this embodiment derives the corrected, lag-free X-ray detection signal $X_k$ promptly from equations A-C constituting a compact recurrence formula.

Here, it is time k=0 that serves as the base point for the recursive computation, i.e. the X-ray non-emission time for the first frame. $X_k$ and $S_{nk}$ at the time of k=0, i.e. initial values, when carrying out the recursive computation, are determined as in the following equation D:

$$X_0 = 0, \; S_{n0} = \gamma_n \cdot Y_0 \quad\quad D$$

where $\gamma_n$: residual rate of component n of certain attenuation time constant $\tau_n$, and $Y_0$: lag signal value remaining at the X-ray non-emission time serving as the base point for the recursive computation.

Figure 10:
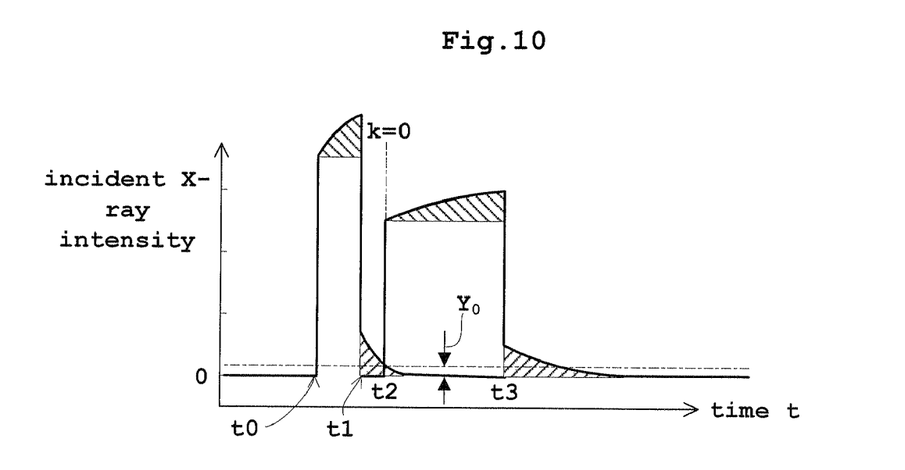
FIG. 10 is a view showing a time lag state with lags of radiography (time lags) superimposed on fluoroscopy.

As shown in FIG. 10, for example, when a lag of the radiography in time t0-t1 is superimposed on fluoroscopy, a residual lag (lag signal value) due to a lag-behind part generated by the radiography in time t0-t1 exists even at the X-ray non-emission time (see k=0 in FIG. 10) which is the base point for the recursive computation. That is, the initial value $Y_0$ of X-ray detection signal $Y_k$ is not 0 even at the X-ray non-emission time.

Then, initial values for the recursive computation are set according to equation D, i.e. $X_0=0$, $S_{n0}=\gamma_n \cdot Y_0$ ($Y_0$: lag signal value remaining at the X-ray non-emission time serving as the base point for the recursive computation). A corrected X-ray detection signal $X_k$ is obtained by removing the lag-behind part based on the impulse response derived from equations A-C with conditions of the initial values determined from equation D.

The above description of equations A-D concerns the data bus lines 29 subjected to the recursive computation. For the data bus lines 29 exempted from the recursive computation, lag-behind parts are removed as follows to obtain corrected X-ray detection signals. Assuming results of the recursive computation carried out for the data bus lines 29 subjected to the recursive computation to be $\Sigma_{n=1}^{N}[S_{nk}]$ in equation A, an average value of $\Sigma_{n=1}^{N}[S_{nk}]$ for the two data bus lines 29 present at opposite sides of each data bus line 29 exempted from the recursive computation is used to remove lag-behind parts and obtain corrected X-ray detection signals. That is, corrected X-ray detection signals are obtained for each data bus line 29 exempted from the recursive computation by using, as the second term of equation A, an average value of $\Sigma_{n=1}^{N}[S_{nk}]$ for the above two data bus lines 29 present at opposite sides, instead of using $\Sigma_{n=1}^{N}[S_{nk}]$ in the second term of equation A. And equations B-D are not used for the data bus lines 29 exempted from the recursive computation.

With the apparatus in this embodiment, the analog-to-digital converter 3, detection signal processor 4, X-ray emission controller 6, irradiating and detecting system movement controller 9, time lag remover 11 and pixel group sorter 12 are operable on instructions and data inputted from an operating unit 13 or on various commands outputted from a main controller 14 with progress of X-ray radiography.

Figure 6:
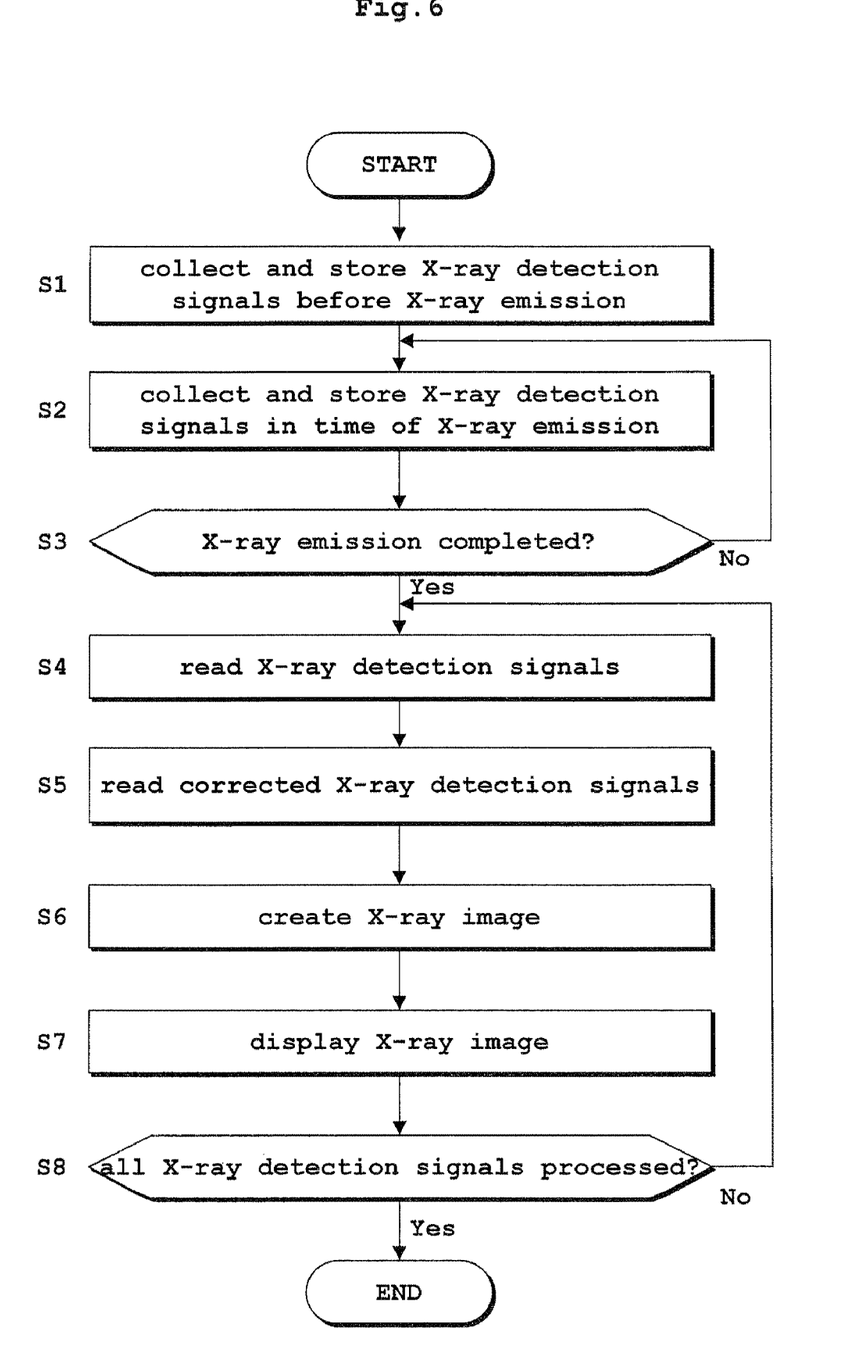
FIG. 6 is a flow chart showing a procedure of an X-ray detection signal processing method according to the embodiment.

Next, an operation for performing X-ray radiography with the apparatus in this embodiment will particularly be described with reference to the drawings. FIG. 6 is a flow chart showing a procedure of an X-ray detection signal processing method according to the embodiment. The radiography herein includes previous radiography as shown in FIG. 10, and current fluoroscopy or radiography.

[Step S1] The analog-to-digital converter 3 starts taking X-ray detection signals $Y_k$ for one X-ray image from the FPD 2 at each period between the sampling time intervals $\Delta t$ (=1/30 second) before X-ray emission. The X-ray detection signals taken are stored in the memory 10.

[Step S2] In parallel with a continuous or intermittent X-ray emission to the patient M initiated by the operator, the analog-to-digital converter 3 continues taking X-ray detection signals $Y_k$ for one X-ray image at each period between the sampling time intervals $\Delta t$ and storing the signals in the memory 10.

[Step S3] When the X-ray emission is completed, the operation proceeds to step S4. When the X-ray emission is uncompleted, the operation returns to step S2.

[Step S4] X-ray detection signals $Y_k$ for one X-ray image collected in one sampling sequence are read from the memory 10.

When this readout of X-ray detection signals is carried out successively in the direction of arrangement of data bus lines 29, the data bus lines 29 are sorted alternately into the locations subjected to the recursive computation and locations exempted from the recursive computation.

[Step S5] For the data bus lines 29 subjected to the recursive computation, the time lag remover 11 performs the recursive computation based on the equations A-C, and derives corrected X-ray detection signals $X_k$, i.e. pixel values, with lag-behind parts removed from the respective X-ray detection signals $Y_k$.

For each data bus line 29 exempted from the recursive computation, the time lag remover 11 derives corrected X-ray detection signals $X_k$ (pixel values) with lag-behind parts removed from the respective X-ray detection signals $Y_k$, by using an average value of $\Sigma_{n=1}^{N}[S_{nk}]$ for the two data bus lines 29 present at opposite sides.

[Step S6] Combining the data bus lines 29 subjected to the recursive computation and the data bus lines 29 exempted from the recursive computation, the detection signal processor 4 creates an X-ray image based on the corrected X-ray detection signals $X_k$ for one sampling sequence (for one X-ray image).

[Step S7] The X-ray image created is displayed on the image monitor 5.

[Step S8] When unprocessed X-ray detection signals $Y_k$ remain in the memory 10, the operation returns to step S4. When no unprocessed X-ray detection signals remain, the X-ray radiography is ended.

With the apparatus in this embodiment, the time lag remover 11 computes the corrected X-ray detection signals $X_k$ corresponding to the X-ray detection signals $Y_k$ for one X-ray image, and the detection signal processor 4 creates an X-ray image, both at each period between the sampling time intervals $\Delta t$ (=1/30 second). That is, the apparatus is constructed also for creating X-ray images one after another at a rate of about 30 images per second, and displaying the created X-ray images continuously. It is thus possible to perform a dynamic display of X-ray images.

Figure 7:
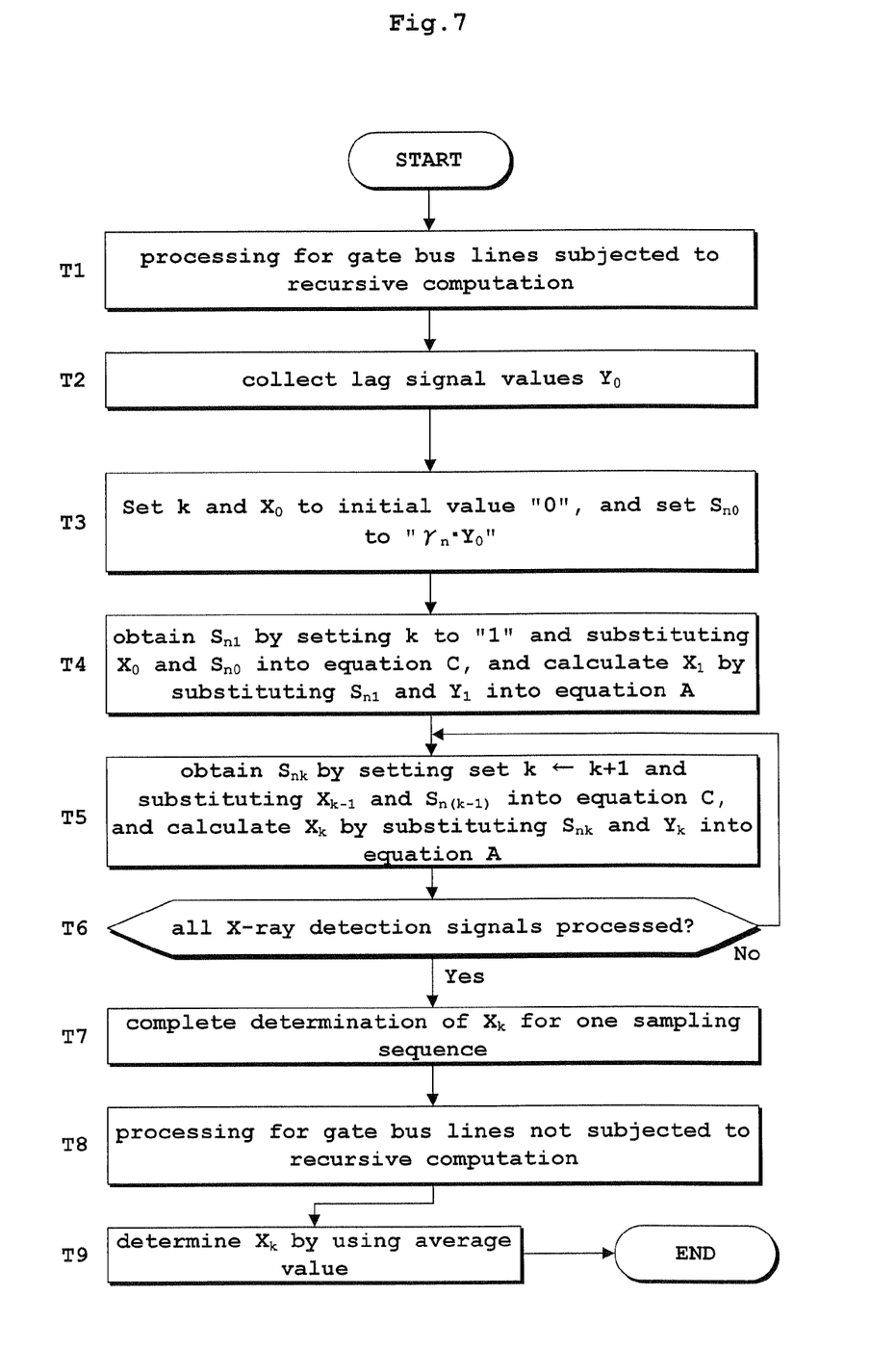
FIG. 7 is a flow chart showing a recursive computation process for time lag removal in the X-ray detection signal processing method according to the embodiment.

Next, the process of recursive computation carried out in step S5 in FIG. 6 by the time lag remover 11 will be described with reference to the flow chart of FIG. 7. FIG. 7 is a flow chart showing a recursive computation process for time lag removal in the X-ray detection signal processing method in this embodiment.

First, the recursive computation is carried out for the data bus lines 29 of the hatched parts in FIG. 8, to remove lag-behind parts and obtain corrected X-ray detection signals (steps T1-T7). Then, a value based on results of the recursive computation (i.e. an average value of $\Sigma_{n=1}^{N}[S_{nk}]$ for the two data bus lines 29 present at opposite sides of each data bus line 29 exempted from the recursive computation) is used to remove lag-behind parts and obtain corrected X-ray detection signals (steps T8 and T9).

[Step T1] Recursive computation is carried out for the data bus lines 29 of the hatched parts in FIG. 8.

[Step T2] Residual lags (lag signal values) due to lag-behind parts generated in past radiography are collected. Specifically, in the first frame, the analog-to-digital converter 3 fetches X-ray detection signals $Y_0$ for one X-ray image from the FPD 2. These X-ray detection signals $Y_0$ are also lag signal value $Y_0$ remaining at the time of X-ray non-emission serving as the base point for recursive computation.

[Step T3] A setting k=0 is made, and $X_0=0$ in equation A is set as initial value. On the other hand, by substituting lag signal value $Y_0$ acquired at step T2 into equation D, $S_{n0}$ in equation C is calculated. It is preferred to set residual rate $\gamma_n$ of component n of certain attenuation time constant $\tau_n$ to satisfy the condition of equation E.

That is, it is preferred to set it to satisfy;

$$\Sigma_{n=1}^{N}[\gamma_n] \leq 1, 0 \leq \gamma_n \qquad E$$

where $\Sigma_{n=1}^{N}[\gamma_n]$: total of residual rates $\gamma_n$ of component n.

When the total of residual rates $\gamma_n$ of components n exceeds 1, the lag-behind parts will be removed excessively. Conversely, when the total of residual rates $\gamma_n$ of components n is a negative value, there is a possibility that the lag-behind parts are added. Then, the lag-behind parts can be removed neither too much nor too little by making the total of residual rates $\gamma_n$ of components n 0 or more and 1 or less, and making residual rates $\gamma_n$ 0 or more. Equation E may be the following equation E' or the following equation E".

That is, when equation E is the following equation E', equation E is set to satisfy the condition of;

$$\Sigma_{n=1}^{N}[\gamma_n]=1 \qquad E',$$

and each residual rate $\gamma_n$ is set to satisfy the condition of equation F:

$$\gamma_1 = \gamma_2 = \ldots = \gamma_n = \ldots = \gamma_{N-1} = \gamma_N \qquad F$$

Equation F is substituted into equation E' to make $N \cdot \gamma_N = 1$. Therefore, each residual rate $\gamma_n$ becomes $\gamma_N = 1/N$, and each residual rate $\gamma_n$ is equally distributed with number N of exponential functions (with different time constants constituting an impulse response). Thus, equation D is expressed by the following equation D' by substituting $\gamma_N = 1/N$ into $S_{n0} = \gamma_n \cdot Y_0$ of equation D.

That is, equation D is expressed by;

$$S_{n0} = Y_0/N \qquad D'.$$

When the number of exponential functions is three (N=3), $S_{10}$, $S_{20}$ and $S_{30}$ are all set to $Y_0/3$ according to equation D.

When equation E is the following equation E", equation E is set to satisfy the condition of;

$$\Sigma_{n=1}^{N}[\gamma_n]<1 \qquad E",$$

and residual rate $\gamma_M$ in component m of certain attenuation time constant $\tau_m$ and other residual rate $\gamma_N$ to satisfy equation G:

$$0<\gamma_M<1, \gamma_N=0 \qquad G$$

When the number of exponential functions is three (N=3), residual rate $\gamma_2$ in component 2 of attenuation time constant $\tau_2$ satisfies $0<\gamma_2<1$ (e.g. $\gamma_2=0.1$) and the other residual rate satisfies $\gamma_1=\gamma_3=0$, $S_{10}$ and $S_{30}$ are set to 0 according to equation G, and $S_{20}$ is set to $\gamma_2 \cdot Y_0$ (e.g. $\gamma_2=0.1$) according to equation G.

[Step T4] In equations A and C, k=1 is set. $S_{11}$, $S_{21}$ and $S_{31}$ are derived from equation C, i.e. $S_{n1}=\exp(T_1) \cdot \{\alpha_1 \cdot [1-\exp(T_1)] \cdot \exp(T_1) \cdot S_{n0}\}$. Further, a corrected X-ray detection signal $X_1$ is obtained by substituting $S_{11}$, $S_{21}$ and $S_{31}$ derived and X-ray detection signal $Y_1$ into equation A.

[Step T5] After incrementing k by 1 (k=k+1) in equations A and C, $X_{k-1}$ of a preceding time is substituted into equation C, thereby obtaining $S_{1k}$, $S_{2k}$ and $S_{3k}$. Further, corrected X-ray detection signal $X_k$ is obtained by substituting $S_{1k}$, $S_{2k}$ and $S_{3k}$ derived and X-ray detection signal $Y_k$ into equation A.

[Step T6] When there remain unprocessed X-ray detection signals $Y_k$, the operation returns to step T5. When no unprocessed X-ray detection signals $Y_k$ remain, the operation proceeds to the next step T7.

[Step T7] Corrected X-ray detection signals $X_k$ for one sampling sequence (for one X-ray image) are obtained to complete the recursive computation for the one sampling sequence, for the data bus lines 29 subjected to the recursive computation (hatched parts in FIG. 8).

[Step T8] Next, processing is carried out for the data bus line 29 of the blank parts in FIG. 8, without carrying out the recursive computation.

[Step T9] For each k (–1, 2, . . . ), an average value of $\Sigma_{n=1}^{N}[S_{nk}]$ is used as the second term in equation A, to determine corrected X-ray detection signals $X_k$ by substituting X-ray detection signals $Y_k$ into equation A. As in step T6, this step T9 is executed as long as there remain unprocessed X-ray detection signals $Y_k$. When no unprocessed X-ray detection signals $Y_k$ remain, processing is completed for one sampling sequence, for the data bus lines 29 exempted from the recursive computation (blank parts in FIG. 8).

According to the fluoroscopic apparatus in this embodiment, as described above, at least the recursive computation is not carried out for locations exempted from the recursive computation (in this embodiment, data bus lines 29 of the blank parts in FIG. 8). Lag-behind parts can be removed from X-ray detection signals, with a calculation amount for the recursive computation reduced by an amount corresponding to the recursive computation excluded. Since the locations subjected to the recursive computation are reduced, the calculation amount can be reduced without extensively changing the conventional apparatus construction. An advantage is provided also that lag correction, which is a correction for removing lag-behind parts, can be carried out using an increased number of time constant components. Further, this embodiment can improve the yield of FPD 2, with the calculation amount reduced, even if acceptability criteria for long-term lags are relaxed.

In this embodiment, when part of pixel groups arranged in one predetermined direction are regarded as lines, locations exempted from the recursive computation are set to be predetermined lines (in this embodiment, data bus lines 29 of the blank parts in FIG. 8), and locations subjected to the recursive computation are set as lines (in this embodiment, data bus lines 29 of the hatched parts in FIG. 8) other than the predetermined lines. With such settings, a division is made in relation to the lines (here, data bus lines 29), whereby the lines can be divided into the locations subjected to the recursive computation and the locations exempted from the recursive computation.

More specifically, locations exempted from the recursive computation are set as predetermined data bus lines 29 (in this embodiment, data bus lines 29 of the blank parts in FIG. 8), while locations subjected to the recursive computation are set as data bus lines 29 (in this embodiment, data bus lines 29 of the hatched parts in FIG. 8) other than the predetermined data bus lines 29. With such setting, a division is made in relation to the data bus lines 29, whereby the lines can be divided into the locations subjected the recursive computation and the locations exempted from the recursive computation. Since the data bus lines 29 extend along the reading direction, the predetermined data bus lines 29 can easily be sorted out at a reading time (step S4 in this embodiment). In this embodiment, adjacent data bus lines 29 are sorted alternately into the locations exempted from the recursive computation and locations subjected to the recursive computation.

On the other hand, for the locations exempted from the recursive computation (in this embodiment, data bus lines 29 of the blank parts in FIG. 8), this embodiment removes lag-behind parts and obtain corrected X-ray detection signals by using a value based on results of the recursive computation for the locations present adjacent such locations and having undergone the recursive computation (in this embodiment, two data bus lines 29 of the hatched parts in FIG. 8 at both sides of each data bus line 29 of the blank part in FIG. 8). By removing lag-behind parts for the locations exempted from the recursive computation in this way, the effect of lag correction which is a correction for removing lag-behind parts can be secured similarly to the locations having undergone the recursive computation, and the effect is hardly impaired.

More specifically, the value based on results of the recursive computation is an amount of statistics (average value here) based on results of the recursive computation. By removing lag-behind parts using such an amount of statistics, corrected X-ray detection signals can be acquired with increased reliability, also for the locations exempted from the recursive computation.

This invention is not limited to the foregoing embodiment, but may be modified as follows:

(1) The foregoing embodiment employs an FPD as the radiation detecting device. This invention is applicable also to an apparatus having a radiation detecting device other than an FPD that causes time lags in X-ray detection signals.

(2) While the apparatus in the foregoing embodiment is a fluoroscopic apparatus, this invention is applicable also to an apparatus other than the fluoroscopic apparatus, such as an X-ray CT apparatus.

(3) The apparatus in the foregoing embodiment is designed for medical use. This invention is applicable not only to such medical apparatus but also to an apparatus for industrial use such as a nondestructive inspecting apparatus.

(4) The apparatus in the foregoing embodiment uses X rays as radiation. This invention is applicable also to an apparatus using radiation other than X rays (e.g. gamma rays).

(5) In the foregoing embodiment, initial values are determined from equation D. In the absence of residual lags (lag signal values) due to lag-behind parts generated in the radiography at time t0-t1 as shown in FIG. 10, during the X-ray non-emission time which is the base point for recursive computation, $X_0=0$ of equation A and $S_{n0}=0$ of equation C may all be set as initial values before X-ray emission.

(6) In the foregoing embodiment, corrected X-ray detection signals are obtained by removing lag-behind parts based on the impulse response derived from equations A-C. As described with relation to the technique of Patent Document 2 (Unexamined Patent Publication No. 2004-242741), lag-behind parts may be removed based on the impulse response derived from equations a-c.

(7) In the foregoing embodiment, adjacent data bus lines 29 are sorted alternately into locations exempted from the recursive computation and locations subjected to the recursive computation. Locations exempted from the recursive computation and locations subjected to the recursive computation may be repeated alternately such that, for example, the recursive computation is carried out for three or more data bus lines 29 continually adjacent one another, while the recursive computation is not carried out only for one data bus line 29 adjacent these. For example, the recursive computation may be carried out for two or more data bus lines 29 continually adjacent one another, while the recursive computation is not carried out for two or more data bus lines 29 adjacent these. Thus, as long as the locations exempted from the recursive computation are set as predetermined data bus lines 29, and the locations subjected to the recursive computation are set as data bus lines 29 other than the predetermined data bus lines 29, the invention is not limited to a particular setting of the respective data bus lines 29.

(8) In the foregoing embodiment, adjacent data bus lines 29 are sorted alternately into locations exempted from the recursive computation and locations subjected to the recursive computation. When part of pixel groups arranged in one predetermined direction are regarded as lines, locations exempted from the recursive computation may be set to be predetermined lines, and locations subjected to the recursive computation to be lines other than the predetermined lines. Thus, settings may be applied to lines other than the data bus lines 29), and the invention is not limited to particular types of lines. Further, instead of being limited to lines, but, for example, locations for which the recursive computation is carried out and locations for which the recursive computation is not carried out may comprise blocks.

(9) For removing lag-behind parts for locations exempted from the recursive computation by using a value based on results of the recursive computation for the locations present adjacent such locations and having undergone the recursive computation, the foregoing embodiment uses a value based on results of the recursive computation for two data bus lines 29 (the hatched parts in FIG. 8) at both sides of each data bus line 29 (the blank part in FIG. 8) exempted from the recursive computation. Three or more data bus lines 29 having undergone the recursive computation may be selected in the order of closeness to each data bus line 29 exempted from the recursive computation, and a value used may be based on results of the recursive computation for these data bus lines 29.

(10) The foregoing embodiment has been described taking an amount of statistics (average value in the embodiment) based on results of the recursive computation as an example of the value based on results of the recursive computation. Instead of being limited to an amount of statistics, the value based on results of the recursive computation may, for example, be results of the recursive computation multiplied by a coefficient less than 1.

(11) In the foregoing embodiment, one example of amount of statistics based on results of the recursive computation is an average value. As long as it is an amount of statistics normally used, it is not limited to an average value. For example, a median value of results of the recursive computation, a mode value of results of the recursive computation, or a weighted average efficiency of results of the recursive computation, is acceptable.

INDUSTRIAL UTILITY

As described above, this invention is suitable for a radiographic apparatus having a flat panel X-ray detector (FPD).

The invention claimed is:

1. A radiographic apparatus for obtaining radiographic images based on radiation detection signals, comprising a radiation emitting device for emitting radiation toward an object under examination, a radiation detecting device for detecting radiation transmitted through the object under examination, and a signal sampling device for taking radiation detection signals from the radiation detecting device at predetermined sampling time intervals, said apparatus being constructed to obtain radiographic images based on the radiation detection signals outputted from the radiation detecting device at the predetermined sampling time intervals as radiation is emitted to the object under examination, said apparatus further comprising a time lag removing device for removing lag-behind parts from the radiation detection signals by a recursive computation, on an assumption that a lag-behind part included in each of said radiation detection signals taken at the predetermined sampling time intervals is due to an impulse response formed of a single or a plurality of exponential functions with different attenuation time constants; and a pixel group sorting device for sorting pixel groups consisting of detection pixels respectively corresponding to positions on said radiation detection device, into locations subjected to said recursive computation and locations exempted from the recursive computation; wherein, for the locations subjected to the recursive computation said time lag removing device removes lag-behind parts by the recursive computation to obtain corrected radiation detection signals, and wherein, for the locations exempted from said recursive computation, said time lag removing device removes the lag-behind parts to obtain corrected radiation detection signals by using a value based on results of said recursive computation for the locations present adjacent the locations and having undergone said recursive computation.

2. The radiographic apparatus according to claim 1, wherein, when part of pixel groups arranged in one predetermined direction are regarded as lines, said pixel group sorting device sets the locations exempted from said recursive computation as predetermined lines, and sets the locations subjected to said recursive computation as lines other than said predetermined lines.

3. The radiographic apparatus according to claim 2, wherein said radiation detection device has a two-dimensional arrangement of a plurality of radiation detecting elements respectively corresponding to pixels, a plurality of gate bus lines connected to the respective radiation detecting elements for switching control of said radiation detecting elements, and data bus lines extending perpendicular to said gate bus lines and connected to the respective radiation detecting elements for reading said radiation detection signals from the radiation detecting elements, said pixel group sorting device setting the locations exempted from said recursive computation as predetermined data bus lines, and setting the locations subjected to said recursive computation as data bus lines other than said predetermined data bus lines.

4. The radiographic apparatus according to claim 3, wherein said pixel group sorting device sorts adjacent data bus lines alternately into the locations exempted from said recursive computation and the locations subjected to said recursive computation.

5. The radiographic apparatus according to claim 1, wherein the value based on results of said recursive computation is an amount of statistics based on results of the recursive computation.

6. The radiographic apparatus according to claim 5, wherein said amount of statistics is an average value of results of the recursive computation.

7. The radiographic apparatus according to claim 6, wherein, for the locations subjected to said recursive computation, the recursive computation is carried out for removing the lag-behind parts from the radiation detection signals, based on the following equations A-C:

$$X_k = Y_k - \Sigma_{n=1}^{N}[S_{nk}] \qquad \text{A}$$

$$T_n = -\Delta t/\tau_n \qquad \text{B}$$

$$S_{nk} = \exp(T_n) \cdot \{\alpha_n \cdot [1-\exp(T_n)] \cdot \exp(T_n) \cdot S_{n(k-1)}\} \qquad \text{C}$$

where $\Delta t$: the sampling time interval;

k: a subscript representing a k-th point of time in a sampling time series;

$Y_k$: a radiation detection signal taken at the k-th sampling time;

$X_k$: a corrected radiation detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n;

to determine the initial values for the recursive computation as in the following equation D:

$$X_0=0, S_{n0}=\gamma_n \cdot Y_0 \quad\quad D$$

where $\gamma_n$: residual rate of component n of certain attenuation time constant $\tau_n$, and $Y_0$: lag signal value remaining at the radiation non-emission time serving as the base point for the recursive computation; and to obtain the corrected radiation detection signals by removing the lag-behind parts based on said impulse response derived from said equations A-C with conditions of the initial values determined from said equation D; and for the locations exempted from said recursive computation, assuming results of said recursive computation to be $\Sigma_{n=1}^{N}[S_{nk}]$ in said equation A, an average value of $\Sigma_{n=1}^{N}[S_{nk}]$ for the locations present adjacent the locations and having undergone the recursive computation is used to remove the lag-behind parts and obtain the corrected X-ray detection signals.

8. A radiation detection signal processing method for taking, at predetermined sampling time intervals, radiation detection signals detected after irradiation of an object under examination, and carrying out signal processing to obtain radiographic images based on the radiation detection signals outputted at the sampling time intervals, the radiation detection signal processing method removing lag-behind parts from the radiation detection signals by a recursive computation, on an assumption that a lag-behind part included in each of said radiation detection signals taken at the predetermined sampling time intervals is due to an impulse response formed of a single or a plurality of exponential functions with different attenuation time constants, wherein pixel groups consisting of detection pixels respectively corresponding to positions on a radiation detection device, which detects radiation and outputs said radiation detection signals, are sorted into locations subjected to said recursive computation and locations exempted from the recursive computation; and wherein, for the locations subjected to the recursive computation, lag-behind parts are removed by the recursive computation to obtain corrected radiation detection signals, and wherein, for the locations exempted from said recursive computation, lag-behind parts are removed to obtain corrected radiation detection signals by using a value based on results of said recursive computation for the locations present adjacent the locations and having undergone said recursive computation.

9. The radiation detection signal processing method according to claim 8, wherein, when part of pixel groups arranged in one predetermined direction are regarded as lines, the locations exempted from said recursive computation are set as predetermined lines, and the locations subjected to said recursive computation are set as lines other than said predetermined lines.

10. The radiation detection signal processing method according to claim 9, wherein, when said radiation detection device has a two-dimensional arrangement of a plurality of radiation detecting elements respectively corresponding to pixels, a plurality of gate bus lines connected to the respective radiation detecting elements for switching control of said radiation detecting elements, and data bus lines extending perpendicular to said gate bus lines and connected to the respective radiation detecting elements for reading said radiation detection signals from the radiation detecting elements, the locations exempted from said recursive computation are set as predetermined data bus lines, and the locations subjected to said recursive computation are set as data bus lines other than said predetermined data bus lines.

11. The radiation detection signal processing method according to claim 10, wherein adjacent data bus lines are sorted alternately into the locations exempted from said recursive computation and the locations subjected to said recursive computation.

12. The radiation detection signal processing method according to claim 8, wherein the value based on results of said recursive computation is an amount of statistics based on results of the recursive computation.

13. The radiation detection signal processing method according to claim 12, wherein said amount of statistics is an average value of results of the recursive computation.

14. The radiation detection signal processing method according to claim 13, wherein, for the locations subjected to said recursive computation, the recursive computation is carried out for removing the lag-behind parts from the radiation detection signals, based on the following equations A-C:

$$X_k = Y_k - \Sigma_{n=1}^{N}[S_{nk}] \quad\quad A$$

$$T_n = -\Delta t/\tau_n \quad\quad B$$

$$S_{nk} = \exp(T_n) \cdot \{\alpha_n \cdot [1-\exp(T_n)] \cdot \exp(T_n) \cdot S_{n(k-1)}\} \quad\quad C$$

where $\Delta t$: the sampling time interval;

k: a subscript representing a k-th point of time in a sampling time series;

$Y_k$: a radiation detection signal taken at the k-th sampling time;

$X_k$: a corrected radiation detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n;

to determine the initial values for the recursive computation as in the following equation D:

$$X_0=0, S_{n0}=\gamma_n \cdot Y_0 \quad\quad D$$

where $\gamma_n$: residual rate of component n of certain attenuation time constant $\tau_n$, and $Y_0$: lag signal value remaining at the radiation non-emission time serving as the base point for the recursive computation; and to obtain the corrected radiation detection signals by removing the lag-behind parts based on said impulse response derived from said equations A-C with conditions of the initial values determined from said equation D; and for the locations exempted from said recursive computation, assuming results of said recursive computation to be $\Sigma_{n=1}^{N}[S_{nk}]$ in said equation A, an average value of $\Sigma_{n=1}^{N}[S_{nk}]$ for the locations present adjacent the locations and having undergone the recursive computation is used to remove the lag-behind parts and obtain the corrected X-ray detection signals.

* * * * *